United States Patent
Shao et al.

(10) Patent No.: US 10,585,325 B2
(45) Date of Patent: Mar. 10, 2020

(54) PHOTO-THERMALLY INDUCED POLYMERIZATION INHIBITORS FOR ELECTROPHORETIC MEDIA

(71) Applicant: E Ink California, LLC, Fremont, CA (US)

(72) Inventors: Lin Shao, Fremont, CA (US); Haiyan Gu, Fremont, CA (US); Ming Wang, Fremont, CA (US); Vladimir Sofiyev, Oakland, CA (US)

(73) Assignee: E INK CALIFORNIA, LLC, Fremont, CA (US)

( * ) Notice: Subject to any disclaimer, the term of this patent is extended or adjusted under 35 U.S.C. 154(b) by 96 days.

(21) Appl. No.: 15/904,739

(22) Filed: Feb. 26, 2018

(65) Prior Publication Data

US 2018/0259823 A1   Sep. 13, 2018

Related U.S. Application Data

(60) Provisional application No. 62/469,082, filed on Mar. 9, 2017.

(51) Int. Cl.
  *G02F 1/167* (2019.01)
  *C07C 39/08* (2006.01)
  (Continued)

(52) U.S. Cl.
  CPC .............. *G02F 1/167* (2013.01); *C01G 3/00* (2013.01); *C01G 23/047* (2013.01); *C07C 39/08* (2013.01);
  (Continued)

(58) Field of Classification Search
  CPC .................. G02F 1/167; G02F 1/1681; G02F 2001/1678; C09D 7/65; C09D 7/66;
  (Continued)

(56) References Cited

U.S. PATENT DOCUMENTS 2,800,457 A   7/1957 Barrett et al.
2,999,881 A   9/1961 Gleckler
(Continued)

FOREIGN PATENT DOCUMENTS

CN   101916024 A   12/2010

OTHER PUBLICATIONS

Kitamura, T. et al., "Electrical toner movement for electronic paper-like display", Asia Display/IDW '01, pp. 1517-1520, Paper HCS1-1 (2001).
(Continued)

*Primary Examiner* — Tom V Sheng
(74) *Attorney, Agent, or Firm* — Ioannis Constantinides

(57) ABSTRACT

An electrophoretic medium that may be incorporated into an electrophoretic display includes a dispersion that may be contained in a plurality of microcapsules or microcells or a polymeric continuous phase. The dispersion may include a non-polar fluid, a plurality of first charged particles; and an inhibitor of photo-thermally induced polymerization that inhibits potential cross-linking between the particles and/or the microcells or polymeric continuous phase. The inhibitor may be a compound having an unsaturated hydrocarbon ring and at least one of a hydroxyl group, a carbonyl group, and a nitroso group. The plurality of microcells or polymeric continuous phase and a coating of the particles may include a polymeric material that includes (meth)acrylates.

11 Claims, 1 Drawing Sheet

(51) Int. Cl.
*C07C 50/04* (2006.01)
*C07C 243/06* (2006.01)
*C01G 23/047* (2006.01)
*C09C 1/48* (2006.01)
*C09D 5/44* (2006.01)
*C01G 3/00* (2006.01)
*C09D 7/65* (2018.01)
*C09D 7/40* (2018.01)
*G02F 1/1675* (2019.01)
*G02F 1/1681* (2019.01)

(52) U.S. Cl.
CPC ............ *C07C 50/04* (2013.01); *C07C 243/06* (2013.01); *C09C 1/48* (2013.01); *C09D 5/4411* (2013.01); *C09D 7/65* (2018.01); *C09D 7/66* (2018.01); *G02F 1/1681* (2019.01); *G02F 2001/1678* (2013.01)

(58) Field of Classification Search
CPC ...... C09D 5/4411; C01G 3/00; C01G 23/047; C07C 39/08; C07C 50/04; C07C 243/06; C09C 1/48
See application file for complete search history.

(56) References Cited

U.S. PATENT DOCUMENTS

| | | |
|---|---|---|
| 3,674,651 A | 7/1972 | Otsuki et al. |
| 3,959,358 A | 5/1976 | Jursich |
| 4,001,140 A | 1/1977 | Foris |
| 4,273,672 A | 6/1981 | Vassiliades |
| 6,028,123 A * | 2/2000 | Hirayama ............ C09D 5/4411 522/151 |
| 6,241,921 B1 | 6/2001 | Jacobson |
| 6,518,374 B1 | 2/2003 | Aichinger |
| 6,545,797 B2 | 4/2003 | Chen |
| 6,672,921 B1 | 1/2004 | Liang |
| 6,751,008 B2 | 6/2004 | Liang |
| 6,788,449 B2 | 9/2004 | Liang |
| 6,831,770 B2 | 12/2004 | Liang |
| 6,833,943 B2 | 12/2004 | Liang |
| 6,850,355 B2 | 2/2005 | Liang |
| 6,859,302 B2 | 2/2005 | Liang |
| 6,866,760 B2 | 3/2005 | Paolini, Jr. |
| 6,867,898 B2 | 3/2005 | Liang |
| 6,914,714 B2 | 7/2005 | Chen |
| 6,930,818 B1 | 8/2005 | Liang |
| 6,972,893 B2 | 12/2005 | Chen |
| 6,982,178 B2 | 1/2006 | LeCain et al. |
| 7,002,728 B2 | 2/2006 | Pullen |
| 7,005,468 B2 | 2/2006 | Zang |
| 7,012,600 B2 | 3/2006 | Zehner |
| 7,046,228 B2 | 5/2006 | Liang |
| 7,052,571 B2 | 5/2006 | Wang |
| 7,072,095 B2 | 7/2006 | Liang |
| 7,075,502 B1 | 7/2006 | Drzaic |
| 7,116,318 B2 | 10/2006 | Amundson |
| 7,144,942 B2 | 12/2006 | Zang |
| 7,166,182 B2 | 1/2007 | Pereira |
| 7,170,670 B2 | 1/2007 | Webber |
| 7,236,291 B2 | 6/2007 | Kaga et al. |
| 7,312,784 B2 | 12/2007 | Baucom |
| 7,321,459 B2 | 1/2008 | Masuda |
| 7,339,715 B2 | 3/2008 | Webber |
| 7,374,634 B2 | 5/2008 | Wang |
| 7,385,751 B2 | 6/2008 | Chen |
| 7,408,696 B2 | 8/2008 | Liang |
| 7,417,787 B2 | 8/2008 | Chopra |
| 7,453,445 B2 | 11/2008 | Amundson |
| 7,522,332 B2 | 4/2009 | Liang |
| 7,535,624 B2 | 5/2009 | Amundson et al. |
| 7,557,981 B2 | 7/2009 | Liang |
| 7,560,004 B2 | 7/2009 | Pereira |
| 7,564,614 B2 | 7/2009 | Chen |
| 7,572,491 B2 | 8/2009 | Wang |
| 7,616,374 B2 | 11/2009 | Chen |
| 7,679,814 B2 | 3/2010 | Paolini, Jr. |
| 7,684,108 B2 | 3/2010 | Wang |
| 7,715,087 B2 | 5/2010 | Hou |
| 7,715,088 B2 | 5/2010 | Liang |
| 7,839,564 B2 | 11/2010 | Whitesides et al. |
| 8,009,348 B2 | 8/2011 | Zehner |
| 8,153,354 B2 | 4/2012 | Johnson |
| 8,179,589 B2 | 5/2012 | Wu |
| 8,361,356 B2 | 1/2013 | Zang |
| 8,520,292 B2 | 8/2013 | Liang |
| 8,625,188 B2 | 1/2014 | Wang |
| 8,830,561 B2 | 9/2014 | Zang |
| 9,081,250 B2 | 7/2015 | Liang |
| 9,279,906 B2 | 3/2016 | Kang |
| 9,346,987 B2 | 5/2016 | Wang |
| 9,447,201 B2 | 9/2016 | Kar |
| 2002/0188053 A1 | 12/2002 | Zang |
| 2004/0120024 A1 | 6/2004 | Chen |
| 2004/0155857 A1* | 8/2004 | Duthaler ............... G02F 1/1334 345/107 |
| 2004/0219306 A1 | 11/2004 | Wang |
| 2005/0105161 A1* | 5/2005 | Nakai ............... G02F 1/134309 359/296 |
| 2005/0168799 A1* | 8/2005 | Whitesides ............ B82Y 30/00 359/296 |
| 2007/0066842 A1* | 3/2007 | Kuang .................... C07C 67/62 560/4 |
| 2007/0091061 A1* | 4/2007 | Schlangen ............. G02F 1/167 345/107 |
| 2007/0298248 A1* | 12/2007 | Hongo ..................... C08J 7/047 428/333 |
| 2010/0015557 A1* | 1/2010 | Johnson .................. G02F 1/167 430/322 |
| 2010/0148385 A1* | 6/2010 | Balko ..................... G02F 1/167 264/4.1 |
| 2014/0330053 A1* | 11/2014 | Mo ......................... C08F 2/40 585/3 |
| 2015/0005720 A1 | 1/2015 | Zang |
| 2015/0098124 A1 | 4/2015 | Li |
| 2015/0213765 A1 | 7/2015 | Gates |
| 2015/0277160 A1 | 10/2015 | Laxton |
| 2016/0012710 A1 | 1/2016 | Lu |
| 2016/0109780 A1 | 4/2016 | Liu |
| 2016/0177127 A1* | 6/2016 | Kuriyama ................ C09D 5/00 428/413 |
| 2017/0240751 A1* | 8/2017 | Morikawa ............. B33Y 70/00 |
| 2018/0210312 A1* | 7/2018 | Liu ....................... G02F 1/1675 |
| 2018/0231864 A1* | 8/2018 | Wang ..................... G02F 1/167 |

OTHER PUBLICATIONS

Gutcho, M.H., Microcapsules and MIcroencapsulation Techniques, Noyes Data Corp., Park Ridge NJ, (1976).

Yamaguchi, Y. et al., "Toner display using insulative particles charged triboelectrically", Asia Display/IDW '01, pp. 1729-1730, Paper AMD4-4 (2001).

Vandegaer, J.E. (ed.), "Microencapsulation Processes and Applications", pp. v-x, 1-180 (Plenum Press, New York 1974).

Korean Intellectual Property Office, PCT/US2018/019638, International Search Report and Written Opinion, dated Jun. 8, 2018.

* cited by examiner

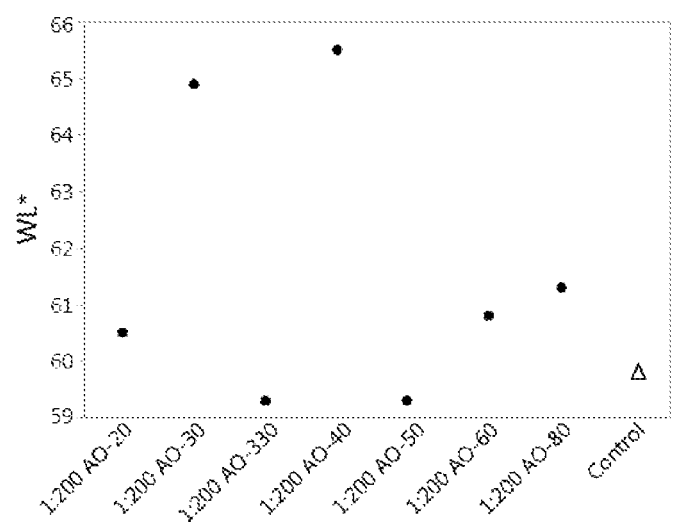

PHOTO-THERMALLY INDUCED POLYMERIZATION INHIBITORS FOR ELECTROPHORETIC MEDIA

CROSS-REFERENCE TO RELATED APPLICATION

This application claims priority to and the benefit of U.S. Provisional Application having Ser. No. 62/469,082, filed on Mar. 9, 2017, the content of which is incorporated by reference herein in its entirety.

BACKGROUND OF INVENTION

This invention relates to electrophoretic displays and additives that inhibit undesired photo-thermally induced polymerization reactions in electrophoretic media to improve the performance of the media when used in a display. For example, the additives of the invention can improve the thermal and optical reliability of the electrophoretic displays.

Particle-based electrophoretic displays have been the subject of intense research and development for a number of years. In such displays, a plurality of charged particles (sometimes referred to as pigment particles) move through a fluid under the influence of an electric field. The electric field is typically provided by a conductive film or a transistor, such as a field-effect transistor. Electrophoretic displays have good brightness and contrast, wide viewing angles, state bistability, and low power consumption when compared with liquid crystal displays. Such electrophoretic displays have slower switching speeds than LCD displays, however, and electrophoretic displays are typically too slow to display real-time video. Additionally, the electrophoretic displays can be sluggish at low temperatures because the viscosity of the fluid limits the movement of the electrophoretic particles. Despite these shortcomings, electrophoretic displays can be found in everyday products such as electronic books (e-readers), mobile phones and mobile phone covers, smart cards, signs, watches, shelf labels, and flash drives.

An electrophoretic image display (EPID) typically comprises a pair of spaced-apart plate-like electrodes. At least one of the electrode plates, typically on the viewing side, is transparent. An electrophoretic fluid composed of a dielectric solvent with charged pigment particles dispersed therein is enclosed between the two electrode plates. An electrophoretic fluid may have one type of charged pigment particles dispersed in a solvent or solvent mixture of a contrasting color. In this case, when a voltage difference is imposed between the two electrode plates, the pigment particles migrate by attraction to the plate of polarity opposite that of the pigment particles. Thus, the color showing at the transparent plate can be either the color of the solvent or the color of the pigment particles. Reversal of plate polarity will cause the particles to migrate to the opposite plate, thereby reversing the color. Alternatively, an electrophoretic fluid may have two types of pigment particles of contrasting colors and carrying opposite charges and the two types of pigment particles are dispersed in a clear solvent or solvent mixture. In this case, when a voltage difference is imposed between the two electrode plates, the two types of pigment particles would move to opposite ends (top or bottom) in a display cell. Thus, one of the colors of the two types of the pigment particles would be seen at the viewing side of the display cell.

Numerous patents and applications assigned to or in the names of the Massachusetts Institute of Technology (MIT), E Ink Corporation, E Ink California, LLC, and related companies describe various technologies used in encapsulated and microcell electrophoretic and other electro-optic media. In a microcell electrophoretic display, the charged pigment particles are retained within a plurality of cavities formed within a carrier medium, typically a polymeric film. The technologies described in these patents and applications include:

(a) Electrophoretic particles, fluids and fluid additives; see for example U.S. Pat. Nos. 7,002,728 and 7,679,814;

(b) Microcell structures, wall materials, and methods of forming microcells; see for example U.S. Pat. Nos. 7,072,095 and 9,279,906;

(d) Methods for filling and sealing microcells; see for example U.S. Pat. Nos. 6,545,797; 6,751,008; 6,788,449; 6,831,770; 6,833,943; 6,859,302; 6,867,898; 6,914,714; 6,972,893; 7,005,468; 7,046,228; 7,052,571; 7,144,942; 7,166,182; 7,374,634; 7,385,751; 7,408,696; 7,522,332; 7,557,981; 7,560,004; 7,564,614; 7,572,491; 7,616,374; 7,684,108; 7,715,087; 7,715,088; 8,179,589; 8,361,356; 8,520,292; 8,625,188; 8,830,561; 9,081,250; and 9,346,987; and U.S. Patent Applications Publication Nos. 2002/0188053; 2004/0120024; 2004/0219306; 2006/0132897; 2006/0164715; 2006/0238489; 2007/0035497; 2007/0036919; 2007/0243332; 2015/0098124; and 2016/0109780;

(e) Films and sub-assemblies containing electro-optic materials; see for example U.S. Pat. Nos. 6,982,178 and 7,839,564;

(f) Backplanes, adhesive layers and other auxiliary layers and methods used in displays; see for example U.S. Pat. Nos. 7,116,318 and 7,535,624;

(g) Color formation and color adjustment; see for example U.S. Pat. Nos. 7,075,502 and 7,839,564;

(h) Methods for driving displays; see for example U.S. Pat. Nos. 7,012,600 and 7,453,445;

(i) Applications of displays; see for example U.S. Pat. Nos. 7,312,784 and 8,009,348; and (j) Non-electrophoretic displays, as described in U.S. Pat. No. 6,241,921 and U.S. Patent Applications Publication No. 2015/0277160; and applications of encapsulation and microcell technology other than displays; see for example U.S. Patent Application Publications Nos. 2015/0005720 and 2016/0012710.

Many commercial electrophoretic media essentially display only two colors, with a gradient between the black and white extremes, known as "grayscale." Such electrophoretic media either use a single type of electrophoretic particle having a first color in a colored fluid having a second, different color (in which case, the first color is displayed when the particles lie adjacent the viewing surface of the display and the second color is displayed when the particles are spaced from the viewing surface), or first and second types of electrophoretic particles having differing first and second colors in an uncolored fluid. In the latter case, the first color is displayed when the first type of particles lie adjacent the viewing surface of the display and the second color is displayed when the second type of particles lie adjacent the viewing surface). Typically the two colors are black and white.

If a full color display is desired, a color filter array may be deposited over the viewing surface of the monochrome (black and white) display. Displays with color filter arrays rely on area sharing and color blending to create color stimuli. The available display area is shared between three or four primary colors such as red/green/blue (RGB) or red/green/blue/white (RGBW), and the filters can be arranged in one-dimensional (stripe) or two-dimensional (2×2) repeat patterns. Other choices of primary colors or more than three primaries are also known in the art. The three (in the case of RGB displays) or four (in the case of RGBW displays) sub-pixels are chosen small enough so that at the intended viewing distance they visually blend together to a single pixel with a uniform color stimulus ('color blending').

Although seemingly simple, electrophoretic media and electrophoretic devices display complex behaviors. For instance, it has been discovered that simple "on/off" voltage pulses are insufficient to achieve high-quality text in electronic readers. Rather, complicated "waveforms" are needed to drive the particles between states and to assure that the new displayed text does not retain a memory of the previous text, i.e., a "ghost." See, for example, U.S. Patent Application No. 20150213765. Compounded with the complexities of the electric fields, the internal phase, i.e., the mixture of particles (pigment) and fluid, can exhibit unexpected behavior due to interactions between charged species and the surrounding environment (such as an encapsulation medium) upon the application of an electric field. Additionally, unexpected behaviors may result from impurities in the fluid, pigments, or encapsulation medium. Accordingly, it is difficult to predict how an electrophoretic display will respond to variations in the internal phase composition.

One particular disadvantage identified in present displays is unwanted reactions between the pigment particles, as well as the potential reactions between pigment particles and the polymeric material used to form the microcells. Pigment particles are commonly coated with polymers in order to impart certain functionality into the surface of the particles. When the polymeric particle coatings or microcell polymeric film contain (meth)acrylate groups, it is possible that the particles may cure together and agglomerate or that the polymeric material of the pigment coatings and microcells may crosslink when exposed to heat or UV light, for example, thus inhibiting/preventing the mobility of the pigment.

Thus, there is a need for improved electrophoretic media and displays in which the media is incorporated.

SUMMARY OF INVENTION

The invention includes improved electrophoretic media formulations. The improved performance results from the inclusion of an inhibitor of photo-thermally induced polymerization that prevents the unwanted crosslinking of the polymeric coatings of pigment particles with each other or with either the polymeric films forming the plurality of microcells of the electrophoretic display or the polymeric material forming the continuous phase of a polymer-dispersed electrophoretic display. The inclusion of some of these inhibitors may also provide additional benefits, such as an improved white state, when included in electrophoretic particle dispersions for reflective displays. In particular, the invention includes electrophoretic media comprising (a) a non-polar fluid, (b) a plurality of first charged particles, and (c) an inhibitor of photo-thermally induced polymerization.

The electrophoretic medium of the invention may include additional types of particles in addition to first charged particles. For example, the electrophoretic medium may include second, third, fourth, fifth or sixth, types of charges particles. The particles may vary in charge, density, hydrophobicity and/or zeta potential. The particles may have different colors, such as magenta, red, orange, yellow, green, cyan, blue, violet, black, and white. The particles may be colorless or transparent. The electrophoretic medium may additionally include surfactants, such as ionic surfactants, i.e., surfactants having a quaternary amine headgroup.

The electrophoretic medium of the invention may be encapsulated, for example in a microcell or a protein coacervate, as discussed in the Background section. In addition, electrophoretic media of the invention can be dispersed in a polymer matrix. The encapsulated or polymer-dispersed electrophoretic media may be incorporated into a front plane laminate (FPL) and/or electro-optic displays as discussed in the Background. Such materials can be used to create electrophoretic image displays (EPID), signs, or architectural materials that will change appearance upon receipt of a signal.

BRIEF DESCRIPTION OF THE FIGURE

The drawing FIGURE depicts one or more implementations in accord with the present concepts, by way of example only, not by way of limitation.

FIG. 1 is a graph plotting the white state (WL*) for various electrophoretic display samples, one control sample and seven samples comprising dispersions containing an inhibitor according to various embodiments of the present invention.

DETAILED DESCRIPTION

The performance of various types of electrophoretic media can be improved by including the inhibitors described herein. For example, the inhibitors of the invention can preserve the contrast between light (on) and dark (off) states for a variety of pigments used in electrophoretic displays after exposure to heat and/or light. Additionally, the inhibitors decrease the incidence and intensity of leftover images after a display has been switched between images, a phenomenon known as "ghosting."

As discussed in the Background, the pigments incorporated into the dispersions of electrophoretic media may include a polymeric shell or coating to impart certain functionality or to provide reactive groups to alter the surface chemistry of the pigment particles. The polymers often include (meth)acrylate groups. Similarly, the polymeric material used to form the microcells or binder that encapsulate the dispersions may also comprise a polymer containing (meth)acrylate groups. As used herein throughout the specification and the claims, "(meth)acrylate" means methacrylate and/or acrylate. The inhibitors incorporated in the electrophoretic media according to the various embodiments of the present invention inhibit and/or prevent the likelihood of crosslinking between the (meth)acrylate groups of the pigments and the microcells that may occur when the electrophoretic display is exposed to heat and/or light. By reducing/eliminating the potential for curing of the pigment particles to each other or to the microcells or binder, the mobility of the pigment particles are preserved, thereby resulting in improved performance for displays that are exposed to heat and/or light over time.

In general, the photo-thermally induced polymerization inhibitors that may be included in the various embodiments of the present invention may include, but are not limited to, compounds having an unsaturated hydrocarbon ring and at least one of a hydroxyl group, a carbonyl group, and a nitroso group. More specifically, the inhibitors may include, but are not limited to phenols/phenoxy-containing compounds (e.g. di-tert-butyl-p-cresol, 2,6-di-tert-butyl-4-methylphenol, 4,4'-methylenebis(2,6-di-tert-butylphenol), 1,5-naphthalenediol, 2,6-di-ter-butyl-p-cresol, 2,2'-methylenebis(6-tert-butyl-p-cresol), 4,4'-biphenyl, 4,4'-butylidenebis(6-tert-butyl-3-methylphenol), 4-tert-butylphenol, 4-methoxyphenol, thiobis(di-sec-amylphenol), and 3,5-di-tert-butyl-4-hydroxybenzyl alcohol), catechols (e.g. 1,4-bis(3,4-dihydroxyphenyl)-2,3-dimethylbutane, 4-methylcatechol, and 4-tert-butyl-5-methoxycatechol), resorcinols (e.g. 4-methylresorcinol, 4-butylresorcinol, 5-tridecylresorcinol, 5-pentadecylresorcinol, and 5-(1,2-dimethylheptyl)-1,3-benzenediol), hydroquinones (e.g. tert-butylhydroquinone, 2,5-di-tert-butylhydroquinone, 2,5-bis-(1,1,3,3-tetramethyl-butyl)-benzene-1,4-diol, methylhydroquinone, trimethylhydroquinone, 2,3-dimethyl-hydroquinone, and 2,5-di-tert-amylhydroquinone), benzoquinones (e.g. 3,5-di-tert-butyl-o-benzoquinone, 2,6-di-tert-butyl-1,4-benzoquinone, 2,5-di-tert-butyl-1,4-benzoquinone, 2-tert-butyl-1,4-benzoquinone, 4-tert-butyl-5-methoxy-o-benzoquinone, 3,6-di-tert-butyl-1,2-benzoquinone, methyl-p-benzoquinone, and 3-t-butyl-5-methoxy-o-benzoquinone), aromatics containing nitroso-groups (e.g. tris (N-nitroso-N-phenylhydroxylamine) aluminum salt, 4-nitrosodimethylaniline, and 1,3,5-Tri-tert-butyl-2-nitrosobenzene), and combinations thereof. The inhibitors may be added to an electrophoretic medium at a concentration of 0.01 to 10% based on the total weight of the dispersion, more preferably the weight percent of additive is 0.1 to 5% based on the total weight of the dispersion.

The inhibitors may be used with electrophoretic media that include functionalized pigments in an organic solvent. The media may be incorporated into displays, or into front plane laminates or inverted front plane laminates that are coupled to a backplane to make a display. Electrophoretic media of the invention, i.e., electrophoretic media containing photo-thermally induced polymerization inhibitors, may include only black and white pigments for use in black/white displays, for example. Electrophoretic media of the invention may also be used in colors displays and contain, for example, three, four, five, six, seven, or eight different types of particles. In one embodiment, an electrophoretic display may be constructed where the particles in the electrophoretic medium includes black, white, and red or black, white, and yellow. Alternatively, the medium may include red, green, and blue particles, or cyan, magenta, and yellow particles, or red, green, blue, and yellow particles.

The term gray state is used herein in its conventional meaning in the imaging art to refer to a state intermediate two extreme optical states of a pixel, and does not necessarily imply a black-white transition between these two extreme states. For example, several of the E Ink patents and published applications referred to below describe electrophoretic displays in which the extreme states are white and deep blue, so that an intermediate gray state would actually be pale blue. Indeed, as already mentioned, the change in optical state may not be a color change at all. The terms black and white may be used hereinafter to refer to the two extreme optical states of a display, and should be understood as normally including extreme optical states which are not strictly black and white, for example the aforementioned white and dark blue states.

The terms bistable and bistability are used herein in their conventional meaning in the art to refer to displays comprising display elements having first and second display states differing in at least one optical property, and such that after any given element has been driven, by means of an addressing pulse of finite duration, to assume either its first or second display state, after the addressing pulse has terminated, that state will persist for at least several times, for example at least four times, the minimum duration of the addressing pulse required to change the state of the display element. It is shown in U.S. Pat. No. 7,170,670 that some particle-based electrophoretic displays capable of gray scale are stable not only in their extreme black and white states but also in their intermediate gray states, and the same is true of some other types of electro-optic displays. This type of display is properly called multi-stable rather than bistable, although for convenience the term bistable may be used herein to cover both bistable and multi-stable displays.

Encapsulation of the internal phase may be accomplished in a number of different ways. Numerous suitable procedures for microencapsulation are detailed in both Microencapsulation, Processes and Applications, (I. E. Vandegaer, ed.), Plenum Press, New York, N.Y. (1974) and Gutcho, Microcapsules and Microencapsulation Techniques, Noyes Data Corp., Park Ridge, N.J. (1976). The processes fall into several general categories, all of which can be applied to the present invention: interfacial polymerization, in situ polymerization, physical processes, such as coextrusion and other phase separation processes, in-liquid curing, and simple/complex coacervation.

Numerous materials and processes should prove useful in formulating displays of the present invention. Useful materials for simple coacervation processes to form the capsule include, but are not limited to, gelatin, poly(vinyl alcohol), poly(vinyl acetate), and cellulosic derivatives, such as, for example, carboxymethylcellulose. Useful materials for complex coacervation processes include, but are not limited to, gelatin, acacia, carageenan, carboxymethylcellulose, hydrolyzed styrene anhydride copolymers, agar, alginate, casein, albumin, methyl vinyl ether co-maleic anhydride, and cellulose phthalate. Useful materials for phase separation processes include, but are not limited to, polystyrene, poly (methyl methacrylate) (PMMA), poly(ethyl methacrylate), poly(butyl methacrylate), ethyl cellulose, poly(vinylpyridine), and polyacrylonitrile. Useful materials for in situ polymerization processes include, but are not limited to, polyhydroxyamides, with aldehydes, melamine, or urea and formaldehyde; water-soluble oligomers of the condensate of melamine, or urea and formaldehyde; and vinyl monomers, such as, for example, styrene, methyl methacrylate (MMA) and acrylonitrile. Finally, useful materials for interfacial polymerization processes include, but are not limited to, diacyl chlorides, such as, for example, sebacoyl, adipoyl, and di- or poly-amines or alcohols, and isocyanates. Useful emulsion polymerization materials may include, but are not limited to, styrene, vinyl acetate, acrylic acid, butyl acrylate, t-butyl acrylate, methyl methacrylate, and butyl methacrylate.

Capsules produced may be dispersed into a curable carrier, resulting in an ink which may be printed or coated on large and arbitrarily shaped or curved surfaces using conventional printing and coating techniques.

In the context of the present invention, one skilled in the art will select an encapsulation procedure and wall material based on the desired capsule properties. These properties include the distribution of capsule radii; electrical, mechanical, diffusion, and optical properties of the capsule wall; and chemical compatibility with the internal phase of the capsule.

The capsule wall generally has a high electrical resistivity. Although it is possible to use walls with relatively low resistivities, this may limit performance in requiring relatively higher addressing voltages. The capsule wall should also be mechanically strong (although if the finished capsule powder is to be dispersed in a curable polymeric binder for coating, mechanical strength is not as critical). The capsule wall should generally not be porous. If, however, it is desired to use an encapsulation procedure that produces porous capsules, these can be overcoated in a post-processing step (i.e., a second encapsulation). Moreover, if the capsules are to be dispersed in a curable binder, the binder will serve to close the pores. The capsule walls should be optically clear. The wall material may, however, be chosen to match the refractive index of the internal phase of the capsule (i.e., the suspending fluid) or a binder in which the capsules are to be dispersed. For some applications (e.g., interposition between two fixed electrodes), monodispersed capsule radii are desirable.

An encapsulation technique that is suited to the present invention involves a polymerization between urea and formaldehyde in an aqueous phase of an oil/water emulsion in the presence of a negatively charged, carboxyl-substituted, linear hydrocarbon polyelectrolyte material. The resulting capsule wall is a urea/formaldehyde copolymer, which discretely encloses the internal phase. The capsule is clear, mechanically strong, and has good resistivity properties.

The related technique of in situ polymerization utilizes an oil/water emulsion, which is formed by dispersing the electrophoretic fluid (i.e., the dielectric liquid containing a suspension of the pigment particles) in an aqueous environment. The monomers polymerize to form a polymer with higher affinity for the internal phase than for the aqueous phase, thus condensing around the emulsified oily droplets. In one in situ polymerization process, urea and formaldehyde condense in the presence of poly(acrylic acid) (see, e.g., U.S. Pat. No. 4,001,140). In other processes, described in U.S. Pat. No. 4,273,672, any of a variety of cross-linking agents borne in aqueous solution is deposited around microscopic oil droplets. Such cross-linking agents include aldehydes, especially formaldehyde, glyoxal, or glutaraldehyde; alum; zirconium salts; and polyisocyanates.

The coacervation approach also utilizes an oil/water emulsion. One or more colloids are coacervated (i.e., agglomerated) out of the aqueous phase and deposited as shells around the oily droplets through control of temperature, pH and/or relative concentrations, thereby creating the microcapsule. Materials suitable for coacervation include gelatins and gum arabic. See, e.g., U.S. Pat. No. 2,800,457.

The interfacial polymerization approach relies on the presence of an oil-soluble monomer in the electrophoretic composition, which once again is present as an emulsion in an aqueous phase. The monomers in the minute hydrophobic droplets react with a monomer introduced into the aqueous phase, polymerizing at the interface between the droplets and the surrounding aqueous medium and forming shells around the droplets. Although the resulting walls are relatively thin and may be permeable, this process does not require the elevated temperatures characteristic of some other processes, and therefore affords greater flexibility in terms of choosing the dielectric liquid.

The electrophoretic medium may alternatively be contained in microfabricated cells, i.e., microcells, such as fabricated by E Ink under the tradename MICROCUP. For example, as described in U.S. Pat. No. 6,930,818, a male mold may be used to imprint a conductive substrate, upon which is formed a transparent conductor film. A layer of a thermoplastic or thermoset precursor is then coated on the conductor film. The thermoplastic or thermoset precursor layer is embossed at a temperature higher than the glass transition temperature of the thermoplastic or thermoset precursor layer by the male mold in the form of a roller, plate or belt. Once formed, the mold is released during or after the precursor layer is hardened to reveal an array of microcells. The hardening of the precursor layer may be accomplished by cooling, cross-linking by radiation, heat or moisture. If the curing of the thermoset precursor is accomplished by UV radiation, UV may radiate onto the transparent conductor film from the bottom or the top of the web as shown in the two figures. Alternatively, UV lamps may be placed inside the mold. In this case, the mold must be transparent to allow the UV light to radiate through the pre-patterned male mold on to the thermoset precursor layer.

The thermoplastic or thermoset precursor for the preparation of the microcells may be multifunctional acrylate or methacrylate, vinylether, epoxide and their oligomers, polymers and the like. A crosslinkable oligomer imparting flexibility, such as urethane acrylate or polyester acrylate, is usually also added to improve the flexure resistance of the embossed micro-cups. The composition may contain polymer, oligomer, monomer and additives or only oligomer, monomer and additives.

In general, the microcells can be of any shape, and their sizes and shapes may vary. The microcells may be of substantially uniform size and shape in one system. However, in order to maximize the optical effect, microcells having a mixture of different shapes and sizes may be produced. For example, microcells filled with a dispersion of the red color may have a different shape or size from the green microcells or the blue microcells. Furthermore, a pixel may consist of different numbers of microcells of different colors. For example, a pixel may consist of a number of small green microcells, a number of large red microcells, and a number of small blue microcells. It is not necessary to have the same shape and number for the three colors.

The openings of the microcells may be round, square, rectangular, hexagonal, or any other shape. The partition area between the openings is preferably kept small in order to achieve a high color saturation and contrast while maintaining desirable mechanical properties. Consequently the honeycomb-shaped opening is preferred over, for example, the circular opening.

For reflective electrophoretic displays, the dimension of each individual microcell may be in the range of about $10^2$ to about $5 \times 10^5$ $\mu m^2$, preferably from about $10^3$ about $5 \times 10^4$ $\mu m^2$. The depth of the microcells is in the range of about 3 to about 100 microns, preferably from about 10 to about 50 microns. The opening to wall ratio is in the range of from about 0.05 to about 100, preferably from about 0.4 to about 20. The distances of the openings usually are in the range of from about 15 to about 450 microns, preferably from about 25 to about 300 microns from edge to edge of the openings.

Many of the aforementioned patents and applications recognize that the walls surrounding the discrete microcapsules in an encapsulated electrophoretic medium could be replaced by a continuous phase, thus producing a so-called polymer-dispersed electrophoretic display, in which the electrophoretic medium comprises a plurality of discrete droplets of an electrophoretic fluid and a continuous phase of a polymeric material, and that the discrete droplets of electrophoretic fluid within such a polymer-dispersed electrophoretic display may be regarded as capsules or microcapsules even though no discrete capsule membrane is associated with each individual droplet; see for example, U.S. Pat. No. 6,866,760. Accordingly, for purposes of the present application, such polymer-dispersed electrophoretic media are regarded as sub-species of encapsulated electrophoretic media.

As noted above, electrophoretic media require the presence of a fluid. In most prior art electrophoretic media, this fluid is a liquid, but electrophoretic media can be produced using gaseous fluids; see, for example, Kitamura, T., et al., Electrical toner movement for electronic paper-like display, IDW Japan, 2001, Paper HCS1-1, and Yamaguchi, Y., et al., Toner display using insulative particles charged triboelectrically, IDW Japan, 2001, Paper AMD4-4). See also U.S. Pat. Nos. 7,321,459 and 7,236,291. Such gas-based electrophoretic media appear to be susceptible to the same types of problems due to particle settling as liquid-based electrophoretic media, when the media are used in an orientation which permits such settling, for example in a sign where the medium is disposed in a vertical plane. Indeed, particle settling appears to be a more serious problem in gas-based electrophoretic media than in liquid-based ones, since the lower viscosity of gaseous suspending fluids as compared with liquid ones allows more rapid settling of the electrophoretic particles.

An encapsulated electrophoretic display typically does not suffer from the clustering and settling failure mode of traditional electrophoretic devices and provides further advantages, such as the ability to print or coat the display on a wide variety of flexible and rigid substrates. (Use of the word printing is intended to include all forms of printing and coating, including, but without limitation: pre-metered coatings such as patch die coating, slot or extrusion coating, slide or cascade coating, curtain coating; roll coating such as knife over roll coating, forward and reverse roll coating; gravure coating; dip coating; spray coating; meniscus coating; spin coating; brush coating; air knife coating; silk screen printing processes; electrostatic printing processes; thermal printing processes; ink jet printing processes; electrophoretic deposition (See U.S. Pat. No. 7,339,715); and other similar techniques.) Thus, the resulting display can be flexible. Further, because the display medium can be printed (using a variety of methods), the display itself can be made inexpensively.

The aforementioned U.S. Pat. Nos. 6,982,178, 6,672,921, 6,788,449, and 6,866,760 describe methods of assembling electrophoretic displays (including an encapsulated electrophoretic display). Essentially, these patents describe a laminate comprising a light-transmissive electrically-conductive layer and a layer of a solid electro-optic medium in electrical contact with the electrically-conductive layer. Typically, the light-transmissive electrically-conductive layer will be carried on a light-transmissive substrate, which is preferably flexible, in the sense that the substrate can be manually wrapped around a drum (say) 10 inches (254 mm) in diameter without permanent deformation. The term light-transmissive is used in this patent and herein to mean that the layer thus designated transmits sufficient light to enable an observer, looking through that layer, to observe the change in display states of the electro-optic medium, which will normally be viewed through the electrically-conductive layer and adjacent substrate (if present); in cases where the electro-optic medium displays a change in reflectivity at non-visible wavelengths, the term light-transmissive should of course be interpreted to refer to transmission of the relevant non-visible wavelengths. The substrate will typically be a polymeric film, and will normally have a thickness in the range of about 1 to about 25 mil (25 to 634 μm), preferably about 2 to about 10 mil (51 to 254 μm). The electrically-conductive layer is conveniently a thin metal or metal oxide layer of, for example, aluminum or indium tin oxide (ITO), or may be a conductive polymer. Poly(ethylene terephthalate) (PET) films coated with aluminum or ITO are available commercially, for example as aluminized Mylar (Mylar is a Registered Trade Mark) from E.I. du Pont de Nemours & Company, Wilmington Del., and such commercial materials may be used with good results in the front plane laminate.

Assembly of an electro-optic display may be effected by attaching the above-described laminate to a backplane with an adhesive under conditions effective to cause the adhesive layer to adhere to the backplane, thereby securing the adhesive layer, layer of electro-optic medium and electrically-conductive layer to the backplane. This process is well-adapted to mass production since the front plane laminate may be mass produced, typically using roll-to-roll coating techniques, and then cut into pieces of any size needed for use with specific backplanes.

In addition to the photo-thermally induced polymerization inhibitors incorporated in the various embodiments of the present invention, electrophoretic media may also include charge control agents (CCAs). For example, pigment particles may be functionalized or surface coated with charged or chargeable groups. The CCAs may be absorbed into the particles, they may be covalently bound to the surface of the particles, and they may exist in a charge complex, or be loosely associated via van der Waals forces. Charge control agents often charge the particles by poorly understood and uncontrolled processes, and can lead to undesirably high conductivity of the electrophoretic medium. Also, because the charge control agent is only physically adsorbed on to the particles and is not bound thereto, changes in conditions may cause partial or complete desorption of the charge control agent from the particles, with consequent undesirable changes in the electrophoretic characteristics of the particles. The desorbed charge control agent might resorb on to other surfaces within the electrophoretic medium, and such resorption has the potential for causing additional problems.

Charge control agents comprising a quaternary amine and an unsaturated polymeric tail comprising monomers of at least 10 carbon atoms in length are preferred. Quaternary amines comprise a quaternary ammonium cation $[NR_1R_2R_3R_4]^+$ bonded to an organic molecule, for example an alkyl group or an aryl group. Quaternary amine charge control agents typically include a long non-polar tail attached to the charged ammonium cation, such as the families of fatty acid quaternary amines offered by Akzo Nobel under the tradenames ARQUAD. The quaternary amine charge control agents may be purchased in a purified form, or the charge control agents may be purchased as a reaction product that has formed a quaternary amine charge control agent. For example, SOLSPERSE 17000 (Lubrizol Corporation), may be purchased as a reaction product of 12-hydroxy-octadecanoic acid homopolymer with N,N-dimethyl-1,3-propanediamine and methylbisulfate. Other useful ionic charge control agents include, but are not limited to, sodium dodecylbenzenesulfonate, metal soap, polybutene succinimide, maleic anhydride copolymers, vinylpyridine copolymers, vinylpyrrolidone copolymer, (meth)acrylic acid copolymers or N,N-dimethylaminoethyl(meth)acrylate copolymers), Alcolec LV30 (soy lecithin), Petrostep B100 (petroleum sulfonate) or B70 (barium sulfonate), OLOA 11000 (succinimide ashless dispersant), OLOA 1200 (polyisobutylene succinimides), Unithox 750 (ethoxylates), Petronate L (sodium sulfonate), Disper BYK 101, 2095, 185, 116, 9077 & 220 and ANTITERRA series.

The charge control agents may be added to the electrophoretic medium at a concentration of greater than 1 g of charge control agent for every 100 g of charged particles.

For example, the charge control agent to charged particle ratio may be 1:30 (wt/wt), e.g., 1:25 (wt/wt), e.g., 1:20 (wt/wt). The charge control agents may have an average molecular weight of greater than 12,000 grams/mole, e.g., greater than 13,000 grams/mole, e.g., greater than 14,000 grams/mole, e.g., greater than 15,000 grams/mole, e.g., greater than 16,000 grams/mole, e.g., greater than 17,000 grams/mole, e.g., greater than 18,000 grams/mole, e.g., greater than 19,000 grams/mole, e.g., greater than 20,000 grams/mole, e.g., greater than 21,000 grams/mole. For example, the average molecular weight of the charge control agent may be between 14,000 grams/mole and 22,000 grams/mole, e.g., between 15,000 grams/mole and 20,000 grams/mole. In some embodiments, the charge control agents have an average molecular weight of about 19,000 grams/mole.

Additional charge control agents may be used, with or without charged groups in polymer coatings, to provide good electrophoretic mobility to the electrophoretic particles. Stabilizers may be used to prevent agglomeration of the electrophoretic particles, as well as prevent the electrophoretic particles from irreversibly depositing onto the capsule wall. Either component can be constructed from materials across a wide range of molecular weights (low molecular weight, oligomeric, or polymeric), and may be a single pure compound or a mixture. An optional charge control agent or charge director may be used. These constituents typically consist of low molecular weight surfactants, polymeric agents, or blends of one or more components and serve to stabilize or otherwise modify the sign and/or magnitude of the charge on the electrophoretic particles. Additional pigment properties which may be relevant are the particle size distribution, the chemical composition, and the lightfastness.

As already indicated, the suspending fluid containing the particles should be chosen based on properties such as density, refractive index, and solubility. A preferred suspending fluid has a low dielectric constant (about 2), high volume resistivity (about 1015 ohm-cm), low viscosity (less than 5 centistokes ("cst")), low toxicity and environmental impact, low water solubility (less than 10 parts per million ("ppm")), and a low refractive index (less than 1.2).

The choice of non-polar fluid may be based on concerns of chemical inertness, density matching to the electrophoretic particle, or chemical compatibility with both the electrophoretic particle and bounding capsule (in the case of encapsulated electrophoretic displays). The viscosity of the fluid should be low when movement of the particles is desired.

Non-polar organic solvents, such as halogenated organic solvents, saturated linear or branched hydrocarbons (e.g. C6-C18 branched alkanes or C7-C10 branched alkanes), silicone oils, and low molecular weight halogen-containing polymers are some useful non-polar fluids. The non-polar fluid may comprise a single fluid. The non-polar fluid will, however, often be a blend of more than one fluid in order to tune its chemical and physical properties. Furthermore, the non-polar fluid may contain additional surface modifiers to modify the surface energy or charge of the electrophoretic particle or bounding capsule. Reactants or solvents for the microencapsulation process (oil soluble monomers, for example) can also be contained in the suspending fluid. Additional charge control agents can also be added to the suspending fluid.

Useful organic solvents include, but are not limited to, epoxides, such as decane epoxide and dodecane epoxide; vinyl ethers, such as cyclohexyl vinyl ether and Decave (Registered Trade Mark of International Flavors & Fragrances, Inc., New York, N.Y.); and aromatic hydrocarbons, such as toluene and naphthalene. Useful halogenated organic solvents include, but are not limited to, tetrafluorodibromoethylene, tetrachloroethylene, trifluorochloroethylene, 1,2,4-trichlorobenzene and carbon tetrachloride. These materials have high densities. Useful hydrocarbons include, but are not limited to, dodecane, tetradecane, the aliphatic hydrocarbons in the Isopar (Registered Trade Mark) series (Exxon, Houston, Tex.), Norpar (Registered Trade Mark) (a series of normal paraffinic liquids), Shell-Sol (Registered Trade Mark) (Shell, Houston, Tex.), and Sol-Trol (Registered Trade Mark) (Shell), naphtha, and other petroleum solvents. These materials usually have low densities. Useful examples of silicone oils include, but are not limited to, octamethyl cyclosiloxane and higher molecular weight cyclic siloxanes, poly(methyl phenyl siloxane), hexamethyldisiloxane, and polydimethylsiloxane. These materials usually have low densities. Useful low molecular weight halogen-containing polymers include, but are not limited to, poly(chlorotrifluoroethylene) polymer (Halogenated Hydrocarbon Inc., River Edge, N.J.), Galden (Registered Trade Mark) (a perfluorinated ether from Ausimont, Morristown, N.J.), or Krytox (Registered Trade Mark) from du Pont (Wilmington, Del.). In a preferred embodiment, the suspending fluid is a poly (chlorotrifluoroethylene) polymer. In a particularly preferred embodiment, this polymer has a degree of polymerization from about 2 to about 10. Many of the above materials are available in a range of viscosities, densities, and boiling points.

It some embodiments, the non-polar fluid will include an optically absorbing dye. This dye must be soluble in the fluid, but will generally be insoluble in the other components of the capsule. There is much flexibility in the choice of dye material. The dye can be a pure compound, or blends of dyes to achieve a particular color, including black. The dyes can be fluorescent, which would produce a display in which the fluorescence properties depend on the position of the particles. The dyes can be photoactive, changing to another color or becoming colorless upon irradiation with either visible or ultraviolet light, providing another means for obtaining an optical response. Dyes could also be polymerizable by, for example, thermal, photochemical or chemical diffusion processes, forming a solid absorbing polymer inside the bounding shell.

A number of dyes already known to those skilled in the art of electrophoretic displays will prove useful. Useful azo dyes include, but are not limited to: the Oil Red dyes, and the Sudan Red and Sudan Black series of dyes. Useful anthraquinone dyes include, but are not limited to: the Oil Blue dyes, and the Macrolex Blue series of dyes. Useful triphenylmethane dyes include, but are not limited to, Michler's hydrol, Malachite Green, Crystal Violet, and Auramine O. The core particle may be of an inorganic pigment such as $TiO_2$, $ZrO_2$, ZnO, $Al_2O_3$, CI pigment black 26 or 28 or the like (e.g., manganese ferrite black spinel or copper chromite black spinel), or an organic pigment such as phthalocyanine blue, phthalocyanine green, diarylide yellow, diarylide AAOT yellow, and quinacridone, azo, rhodamine, perylene pigment series from Sun Chemical, Hansa yellow G particles from Kanto Chemical, and Carbon Lampblack from Fisher or the like.

Particle dispersion stabilizers may also be added to prevent particle flocculation or attachment to the capsule walls. For the typical high resistivity liquids used as suspending fluids in electrophoretic displays, non-aqueous surfactants may be used. These include, but are not limited to, glycol ethers, acetylenic glycols, alkanolamides, sorbitol derivatives, alkyl amines, quaternary amines, imidazolines, dialkyl oxides, and sulfosuccinates.

If a bistable electrophoretic medium is desired, it may be desirable to include in the suspending fluid a polymer having a number average molecular weight in excess of about 20,000, this polymer being essentially non-absorbing on the electrophoretic particles; poly(isobutylene) is a preferred polymer for this purpose. See U.S. Pat. No. 7,170,670, the entire disclosure of which is herein incorporated by reference.

Once encapsulated, the electrophoretic media according to the various embodiments of the present invention may be combined with binders and/or application agents to improve the construction of an electrophoretic display. For example, coating aids can be used to improve the uniformity and quality of the coated or printed electrophoretic ink material. Wetting agents may be added to adjust the interfacial tension at the coating/substrate interface and to adjust the liquid/air surface tension. Wetting agents include, but are not limited to, anionic and cationic surfactants, and nonionic species, such as silicone or fluoropolymer-based materials. Dispersing agents may be used to modify the interfacial tension between the capsules and binder, providing control over flocculation and particle settling.

EXAMPLES

Examples are now given, though by way of illustration only, to show details of preferred electrophoretic media of the present invention.

Example 1

Two microcell films were prepared as described in U.S. Pat. No. 6,930,818, the content of which is incorporated herein by reference in its entirety. Electrophoretic media containing 1:200 (wt/wt) concentration of 2,6-di-tert-butyl-p-cresol (TBPC) or tris(N-nitroso-N-phenylhydroxylamine) aluminum salt (NNNPA) to the electrophoretic particles was prepared for a test display by coating the electrophoretic media onto a front plane laminate having the microcell film and the front plane laminate was subsequently laminated to a back-plane having a TFT array.

The display was first driven to the white state (W) or the black state (K) with a 5 Volt waveform (LV) and then placed in a Qsun chamber for 3 days prior to a testing the performance again. The displays were evaluated for a relative reflectance and color in the light and dark state using an X-rite iOne spectrophotometer with D65 illumination (X-rite, Grand Rapids, Mich.). The data is reported using both CIExyY and CIELAB color space algorithms. The level of ghosting was determined by driving the display between light and dark images and evaluating the amount of residual reflectance when going from light to dark images, and the amount of reduced reflectance when going from dark to light images. In practice, each display was driven between positive and negative checkerboard patterns while the change in L* was measure at several locations, thereby allowing for the collection of many relevant data points in a short amount of time. Results are provided in Table 1.

TABLE 1

LV performance comparison with/without TBPC after Q-sun

| | | | Driven to W state | | Driven to K state | |
|---|---|---|---|---|---|---|
| | | | Sample 1 No TBPC | Sample 2 1:200 TBPC | Sample 1 No TBPC | Sample 2 1:200 TBPC |
| Before 3-day Q-Sun | Contrast | W (%) | 38.6 | 38.2 | 38.1 | 39.0 |
| | | K (%) | 1.9 | 1.9 | 1.9 | 1.9 |
| | Ghosting | W ghosting (ΔL*) | 0.3 | 0.3 | 0.3 | 0.3 |
| | | K ghosting (ΔL*) | 0.5 | 0.7 | 0.2 | 0.4 |
| After 3-day Q-Sun | Change | W-decay | −1.4 | −0.6 | −4.0 | −3.8 |
| | | K--decay | 4.4 | 2.4 | 2.6 | 1.0 |
| | Ghosting | W ghosting (ΔL*) | 0.7 | 0.6 | 0.8 | 0.6 |
| | | K ghosting (ΔL*) | 2.6 | 1.6 | 1.7 | 0.9 |

The results in Table 1 demonstrated that adding TBPC decreased the K decay after Qsun 3-day exposure by approximately 50% and reduced the K ghosting by approximately 40% when added at 1:200 wt/wt. The TBPC also resulted in slightly improved white state reflectivity.

Example 2

The electrophoretic medium was prepared and incorporated into a display sample according to the procedure of Example 1, except that the photo-thermally induced polymerization inhibitor used was tris (N-nitroso-N-phenylhydroxylamine) aluminum salt (NNNPA) instead of TBPC. The samples were then tested using a similar method as Example 1, results provided in Table 3, as well as a modified test in which the display sample was placed in a 60 C chamber for 3 days, results provided in Table 2.

TABLE 2

LV performance comparison with/without NNNPA after exposure to 60 C. heat

|  |  |  | No NNNPA | 1:200 NNNPA |
|---|---|---|---|---|
| Before 60 C. operation | Contrast | W (%) | 38.2 | 37.7 |
|  |  | K (%) | 1.8 | 1.8 |
|  | Ghosting | W ghosting ($\Delta L^*$) | 0.3 | 0.5 |
|  |  | K ghosting ($\Delta L^*$) | 0.4 | 0.4 |
| After 60 C. operation | Change | W-decay | −3.0 | −2.0 |
|  |  | K-decay | 3.2 | 1.5 |
|  | Ghosting | W ghosting ($\Delta L^*$) | 0.4 | 0.6 |
|  |  | K ghosting ($\Delta L^*$) | 0.4 | 0.4 |

TABLE 3

LV performance comparison with/without NNNPA after exposure in Q-sun chamber

|  |  |  | Driven to W state | | Driven to K state | |
|---|---|---|---|---|---|---|
|  |  |  | No NNNPA | 1:200 NNNPA | No NNNPA | 1:200 NNNPA |
| Before 3-day Q-Sun | Contrast | W (%) | 37.8 | 37.6 | 38.2 | 37.6 |
|  |  | K (%) | 1.8 | 1.7 | 1.7 | 1.7 |
|  | Ghosting | W ghosting ($\Delta L^*$) | 0.3 | 0.4 | 0.3 | 0.5 |
|  |  | K ghosting ($\Delta L^*$) | 0.5 | 0.4 | 0.5 | 0.4 |
| After 3-day Q-Sun | Change | W-decay | −0.6 | −1.1 | −3.9 | −2.0 |
|  |  | K-decay | 4.6 | 3.3 | 4.1 | 1.9 |
|  | Ghosting | W ghosting ($\Delta L^*$) | 0.4 | 0.5 | 0.6 | 0.6 |
|  |  | K ghosting ($\Delta L^*$) | 2.7 | 1.3 | 1.8 | 1.2 |

The results in Tables 2 and 3 above demonstrate that adding 1:200 wt/wt NNNPA improved the W state by 33% and K state by 52% after the 3-day 60 C operation test. Adding 1:200 wt/wt NNNPA also improved the W state by 49% and K state by 53% after the Qsun exposure test when driven to the K state. The K ghosting levels after Qsun exposure were also improved by 52% and by 33% when driven to W state and K state, respectively, during Qsun exposure.

Example 3

Microcell films were prepared according to the procedure noted in Example 1. Display samples were prepared by coating eight different formulations of electrophoretic media onto a front plane laminate having the microcell film and the front plane laminate was subsequently laminated to an ITO glass backplane. All eight electrophoretic medium formulations contained white, black, red, and yellow electrophoretic particles. The Control sample contained no inhibitor while each of the remaining seven samples contained 1:200 (wt/wt) concentration of one of the following inhibitors to electrophoretic particles: tris(3,5-di-tert-butyl-4-hydroxybenzyl) isocyanurate ("AO-20"), 4,4',4"-(1-methylpropanyl-3-ylidene)tris[6-tert-butyl-m-cresol] ("AO-30"), 1,3,5-trimethyl-2,4,6-tris(3,5-di-tert-butyl-4-hydroxybenzyl)benzene ("AO-330"), 4,4'-butylidenebis(6-tert-butyl-m-cresol) ("AO-40"), octadecyl 3-(3,5-di-tert-butyl-4-hydroxyphenyl) propionate ("AO-50"), pentaerythritol tetrakis(3,5-di-tert-butyl-4-hydroxyhydrocinnamate) ("AO-60"), and 3,9-bis 1,1-dimethyl-2-(3-tert-butyl-4-hydroxy-5-methylphenyl) propionyloxyethyl-2,4,8,10-tetraoxaspiro[5.5]undecane ("AO-80"). The displays were evaluated for a relative reflectance and color in the light and dark state using an X-rite iOne spectrophotometer with D65 illumination (X-rite, Grand Rapids, Mich.). The data is reported using CIELAB color space algorithm.

As illustrated in FIG. 1, the AO-30 and AO-40 samples exhibited improved light states when compared to the other samples. Thus, the inclusion of certain polymerization inhibitors may provide additional benefits, such as an improved white state, when included in electrophoretic particle dispersions for reflective displays.

As indicated above, the present invention provides photothermally induced polymerization inhibitors that can be included in electrophoretic media to improve the performance of the media.

It will be apparent to those skilled in the art that numerous changes and modifications can be made in the specific embodiments of the invention described above without departing from the scope of the invention. Accordingly, the whole of the foregoing description is to be interpreted in an illustrative and not in a limitative sense.

We claim:

1. An electrophoretic medium comprising a dispersion, the dispersion comprising:
   (a) a non-polar fluid;
   (b) a plurality of first charged particles; and
   (c) an inhibitor of photo-thermally induced polymerization, wherein the inhibitor is selected from the group consisting of 2, 6-di-tert-butyl-p-cresol, tris (N-nitroso-N-phenylhydroxylamine) aluminum salt, 4,4',4"-(1-methylpropanyl-3-ylidene)tris[6-tert-butyl-m-cresol], and 4,4'-butylidenebis(6-tert-butyl-m-cresol).

2. The electrophoretic medium of claim 1, wherein the first charged particles comprise a polymeric coating containing (meth)acrylate groups.

3. The electrophoretic medium of claim 2, wherein the dispersion is encapsulated within a plurality of microcells or polymeric continuous phase comprising a polymeric material containing (meth)acrylate groups.

4. The electrophoretic medium of claim 1, wherein the dispersion is encapsulated.

5. The electrophoretic medium of claim 4, wherein the dispersion is encapsulated within a plurality of microcells or polymeric continuous phase comprising a polymeric material containing (meth)acrylate groups.

6. The electrophoretic medium of claim 1, further comprising a plurality of second charged particles dispersed in the non-polar fluid, wherein the first and second charged particles have opposite charges, and at least one of the first and second charged particles comprises a polymeric coating containing (meth)acrylate groups.

7. The electrophoretic medium of claim 6, wherein the dispersion is encapsulated within a plurality of microcells or polymeric continuous phase comprising a polymeric material containing (meth)acrylate groups.

8. The electrophoretic medium of claim 1, wherein the first charged particles comprise titania, carbon black, or copper chromite.

9. The electrophoretic medium of claim 1, wherein the weight percent of the inhibitor is 0.01 to 10% based on the total weight of the dispersion.

10. The electrophoretic medium of claim 1, wherein the weight percent of the inhibitor is 0.1 to 5% based on the total weight of the dispersion.

11. The electrophoretic medium of claim 1 further comprising a plurality of second charged particles and a plurality of third charged particles dispersed in the non-polar fluid, wherein each of the first, second, or third charged particles are a different color selected from red, green, blue, cyan, yellow, and magenta.

* * * * *